(12) United States Patent
Huang et al.

(10) Patent No.: US 12,571,792 B2
(45) Date of Patent: Mar. 10, 2026

(54) HUMAN CEREBRAL CORTICAL ORGANOID CHIP, METHOD FOR THREE-DIMENSIONAL (3D) PRINTING THEREOF AND APPLICATION THEREOF

(71) Applicants: SHANDONG UNIVERSITY, Shandong (CN); YANSHAN UNIVERSITY, Hebei (CN)

(72) Inventors: Chuanzhen Huang, Qinhuangdao (CN); Zhuang Chen, Jinan (CN); Hanlian Liu, Jinan (CN); Peng Yao, Jinan (CN); Dun Liu, Jinan (CN); Hongtao Zhu, Jinan (CN); Bin Zou, Jinan (CN); Zhen Wang, Qinhuangdao (CN); Jun Wang, Qinhuangdao (CN); Longhua Xu, Qinhuangdao (CN); Shuiquan Huang, Qinhuangdao (CN); Meina Qu, Qinhuangdao (CN); Zhengkai Xu, Qinhuangdao (CN); Minting Wang, Qinhuangdao (CN); Yabin Guan, Qinhuangdao (CN)

(73) Assignees: SHANDONG UNIVERSITY, Jinan (CN); YANSHAN UNIVERSITY, Qinhuangdao (CN)

( * ) Notice: Subject to any disclaimer, the term of this patent is extended or adjusted under 35 U.S.C. 154(b) by 613 days.

(21) Appl. No.: 18/182,091

(22) Filed: Mar. 10, 2023

(65) Prior Publication Data

US 2024/0302352 A1 Sep. 12, 2024

(30) Foreign Application Priority Data

Dec. 23, 2022 (CN) .......................... 202211662613.2

(51) Int. Cl.
*G01N 33/50* (2006.01)
*B33Y 70/00* (2020.01)
(Continued)

(52) U.S. Cl.
CPC .......... *G01N 33/5082* (2013.01); *B33Y 70/00* (2014.12); *B33Y 80/00* (2014.12);
(Continued)

(58) Field of Classification Search
CPC .......... G01N 33/5082; G01N 33/5058; G01N 2500/10; B33Y 70/00; B33Y 80/00;
(Continued)

(56) References Cited

U.S. PATENT DOCUMENTS

2018/0355299 A1* 12/2018 Guenat .................. C12M 35/08
2021/0095260 A1* 4/2021 Knoblich ............. C12N 5/0697

FOREIGN PATENT DOCUMENTS

CN 109337813 A 2/2019
CN 111269833 A * 6/2020 ........... C12N 5/0676
(Continued)

*Primary Examiner* — John McGuirk
(74) *Attorney, Agent, or Firm* — Oliff PLC

(57) ABSTRACT

A method of rapid constructing human cerebral cortical organoids by 3D bioprinting and an application including preparing microfluidic chips, preparation of hydrogel of human cerebral cortical organoids, and printing of human cerebral cortical organoids. The microfluidic chip comprises a mixed-flow channel layer, liquid pool layer, microporous array layer, human cerebral cortical organoid culture layer, and culture medium recovery layer; the human cerebral cortical organoid hydrogel has gelatin, alginate, and hyaluronic acid; printing directly human cerebral cortical organoids in microfluidic chips by FRESH printing method, obtaining human cerebral cortical organoid chips after packaging. The application directly constructs large-scale human cerebral cortex-like with three layers of mutually connected structures in situ in organ chip through 3D bioprinting, simulates cerebrospinal fluid circulation through perfusion culture.

8 Claims, 5 Drawing Sheets

(51) Int. Cl.

| | | |
|---|---|---|
| *B33Y 80/00* | (2015.01) | |
| *C12N 5/079* | (2010.01) | |
| *C12N 5/0793* | (2010.01) | |
| *C12N 5/0797* | (2010.01) | |

(52) U.S. Cl.
CPC ......... *C12N 5/0618* (2013.01); *C12N 5/0619* (2013.01); *C12N 5/0623* (2013.01); *C12N 2501/13* (2013.01); *C12N 2513/00* (2013.01); *C12N 2533/54* (2013.01); *C12N 2533/74* (2013.01)

(58) Field of Classification Search
CPC .... B33Y 10/00; C12N 5/0618; C12N 5/0619; C12N 5/0623; C12N 2501/13; C12N 2513/00; C12N 2533/54; C12N 2533/74; C12N 5/0697; C12N 2501/90; C12N 2501/905; C12N 2501/998; C12M 23/16; C12M 21/08; A61L 27/20; A61L 27/222; A61L 27/383; A61L 27/3878; A61L 27/3895; A61L 27/52; A61L 27/56; A61L 2430/32; A61L 2430/40; B01L 3/5027
See application file for complete search history.

(56) References Cited

FOREIGN PATENT DOCUMENTS

| | | | | | |
|---|---|---|---|---|---|
| CN | 113878955 A | * | 1/2022 | ............... | B32B 5/08 |
| CN | 114854584 A | * | 8/2022 | ............ | C12M 25/04 |

* cited by examiner

HUMAN CEREBRAL CORTICAL ORGANOID CHIP, METHOD FOR THREE-DIMENSIONAL (3D) PRINTING THEREOF AND APPLICATION THEREOF

CROSS-REFERENCES TO RELATED APPLICATIONS

This application claims priority benefits to Chinese Patent Application No. 202211662613.2, filed 23 Dec. 2022, the contents of which are incorporated herein by reference.

TECHNICAL FIELD

The present invention relates to the field of microfluidic chips, and in particular to a human cerebral cortical organoid chip, a method for rapid construction of human cerebral cortical organoids by 3D bioprinting and an application thereof.

BACKGROUND

The information disclosed in the background technology of the invention is intended to increase the understanding of the overall background of the invention, and the disclosure should not necessarily be regarded as admitting or implying in any form that the information has become a prior art known to ordinary technicians in the art.

Organ-on-a-chip, a breakthrough in the field of stem cell research in recent years, is an organ physiological micro-system constructed on a slide-sized chip that contains key elements of the organ microenvironment such as living cells, tissue interfaces, biofluids, and mechanical forces. As a new technology, organ-on-a-chip technology has attracted more and more attention and has a wide range of applications in life science, drug research, personalized medicine, and toxicity prediction.

The patent CN201811226234.2 disclosed a system and a method suitable for culturing and real-time monitoring of biological tissue, comprising: a 3D bioprinter, an organ chip, a connecting base, a drive system and an auxiliary system, wherein the organ chip is connected with the drive system through the connecting base; the 3D bioprinter is used for constructing 3D bioprinting tissue-like; the organ chip is used for accommodating a medium and the 3D bioprinting tissue-like and culturing the 3D bioprinting tissue-like; the connection base is used for accommodating the organ chip and connected with the drive system; the drive system is used for driving the medium to flow in the organ chip; the auxiliary system is used for monitoring the state of the 3D bioprinting tissue-like; a main body of the organ chip further comprises: a hard top layer, a microfluidic-channel layer, a transparent bottom layer, a sensing chip, wherein the microfluidic-channel layer being provided between the hard top layer and the transparent bottom layer, the sensing chip being in contact with a culture medium of the organ chip main body; the hard top layer comprises at least one culture chamber, one gas channel, one top groove, one bottom groove and one detection area; the bottom groove is used for accommodating the microfluidic-channel layer; the microfluidic-channel layer comprises at least one culture chamber, one microfluidic channel, one drive groove, one storage pool groove, one split groove and one fenestrated valve, wherein the at least one culture chamber, one drive groove, one storage pool groove, and one split groove are connected through the microfluidic-channel; the fenestrated valve separates the split groove; wherein a transfer unit is matched with the at least one culture chamber in the hard top layer and the at least one culture chamber in the microfluidic-channel layer.

The chip constructed by the above patent has a complex structure, difficult practical application, cannot support the renewal of culture medium, could cause the accumulation of toxic substances, and is difficult to support long-term culture. Crucially, the printing method and organ chip described in the patent cannot support the printing of soft tissues, especially the human cerebral cortical organoids.

The human cerebral cortex has the characteristics of low elastic modulus and high dissipation, and the nerve cells have particularly strict requirements on the living environment. It is still difficult to prepare a kind of bioink of human cerebral cortical organoids with good comprehensive properties for 3D bioprinting.

SUMMARY

To solve the problems in the prior art, the present invention provides a human cerebral cortical organoid chip, a method of 3D bioprinting human cerebral cortical organoids, and an application thereof. The present invention mainly designs a human cerebral cortical organoid chip, and directly prints the human cerebral cortical organoid with a three-layer structure in situ in the chip in combination with the 3D bioprinting method.

Specifically, the present invention provides the following technical features, and the combination of one or more of the following technical features constitutes the technical solution of the present invention.

It is a first aspect of the present invention to provide a human cerebral cortical organoid chip, comprising from top to bottom a mixed-flow channel layer, a liquid pool layer, a microporous array layer, a human cerebral cortical organoid culture layer, and a culture medium recovery layer; wherein, adjacent layers are sealed by a sealing ring;

the mixed-flow channel layer comprises a culture medium input port, a mixed-flow channel, a first blind via, and a culture medium recovery port;

the liquid pool layer comprises a culture medium storage pool, a first through-hole, and a second through-hole; wherein the culture medium input port is used for inputting the culture medium, the mixed-flow channel mixes the different components of culture medium evenly, and the mixed culture medium is inputted into the culture medium storage pool in the liquid pool layer through the first blind via and the first through-hole;

the microporous array layer is provided with a third through-hole;

the human cerebral cortical organoid culture layer comprises a culture chamber, a fourth through-hole, and a microporous array; the culture chamber being a human cerebral cortical organoid culture chamber; the culture medium flows from the culture chamber through the microporous array layer into the medium recovery layer; the microporous array layer is used for allowing the medium to pass slowly; and the culture medium recovery layer is provided with a culture medium recovery pool and a second blind via, and a bottom of the culture medium recovery pool is provided with a slope, and the culture medium passes through the second blind via, the fourth through-hole, the third through-hole, and the second through-hole in turn and then passes through the culture medium recovery port to complete a recovery cycle.

Preferably, the slope of the bottom of the culture medium recovery pool is 1°.

Preferably, the material of the human cerebral cortical organoid chip is ordinary flat glass.

Preferably, rubber sealing rings with the same shapes of the layers are sandwiched between the layers of a five-layer structure and are used for sealing between the layers.

Preferably, a PET porous membrane is covered under the microporous array layer and is used for buffering the pressure of the culture medium on the human cerebral cortical organoid.

It is a second aspect of the present invention, based on the human cerebral cortical organoid chip, to provide a method for in situ 3D bioprinting human cerebral cortical organoids in a human cerebral cortical organoid chip, wherein connecting a culture medium recovery layer and a human cerebral cortical organoid culture layer with studs and then fixing them on a printing platform; injecting a gelatin support bath into a culture chamber; storing a cell-laden bioink in a syringe of a 3D bioprinter; in situ printing the human cerebral cortical organoid in the gelatin support bath in the culture chamber using the 3D extrusion bioprinter; and, after the printing is completed, in situ packaging the chip, and then perfusing with the culture medium for culturing.

Further, before assembling the chip, sterilizing the human cerebral cortical organoid chip by using 120° C. high-temperature and high-pressure sterilization.

As a further technical solution, after the printing is completed, scraping off the excess gelatin support bath with a spatula, and sequentially assembling a microporous array layer, a liquid pool layer, and a mixed-flow channel layer; introducing the culture medium into a culture medium input port; and, placing the chip in an incubator for culturing.

As a further technical solution, components of the cell-laden bioink comprise alginate, gelatin, and hyaluronic acid.

As a further technical solution, a method of preparing the bioink comprises the following steps: dissolving alginate, gelatin, and hyaluronic acid respectively in buffer solutions to obtain a bioink precursor solution, and then dispersing the cells evenly into the bioink precursor solution to obtain the cell-laden bioink.

As a further technical solution, the method of preparing the cell-laden bioink specifically comprises:

Step 1: dissolving sodium alginate in 1×PBS (phosphate buffered saline), stirring for a set time at a set temperature, and degassing using an ultrasonic dispersion instrument to obtain an alginate solution;

Step 2: dissolving gelatin and hyaluronic acid in 1×PBS, stirring for a set time at a set temperature, and degassing using the ultrasonic dispersion instrument to obtain a gelatin composite solution;

Step 3: irradiating the alginate solution with ultraviolet (UV) light for a set time to sterilize, and sterilizing by filtration the gelatin composite solution using a sterilizing filter at a set temperature environment; and Step 4: mixing the alginate solution with the gelatin composite solution at a set temperature in a 1:1 ratio to obtain a bioink precursor solution, and dispersing the cells evenly into the bioink precursor solution to obtain the cell-laden bioink.

It is a third aspect of the present invention, based on the printing method described above, also to provide a human cerebral cortical organoid obtained using the method of 3D bioprinting the human cerebral cortical organoid described above, comprising a structure formed by three layers connected, wherein the top layer is a tissue plate with nerve fibers arranged longitudinally, the middle layer is a sparse nerve fiber bundle, and the bottom layer is a nerve tissue plate with nerve fibers arranged transversely.

It is a fourth aspect of the present invention also to provide an application of a human cerebral cortical organoid described above in neurologic drug screening.

It is a fifth aspect of the present invention also to provide an application of a bioink described above in materials for repairing neural damage or in the preparation of human cerebral cortical organoids.

One or More Technical Solutions Provided in the Present Invention have at Least the Following Technical Effects or Advantages 1. The present invention proposed the human cerebral cortical organoid chip, simulating a structure of a cranial cavity of the human brain by using a double-layer porous membrane separating the culture chamber, and providing low shear stress by connecting the external flowing culture medium to promote maturation of human cerebral cortical organoids; the chip is small in size, low in processing cost, and easy to apply.
2. In situ constructing directly the human cerebral cortical organoid with complex structure in the organ chip by FRESH (Freeform Reversible Embedding of Suspended Hydrogels) printing method, the organ chip can be directly packaged and perfused for culture after printing; and the flow of the culture medium simulates the circulation of cerebrospinal fluid and has the ability of long-term culture. The whole printing process is carried out in the cell-friendly temperature range. And, in the present invention, the bioink for the human cerebral cortical organoid has adjustable elastic modulus and porosity to support the survival of neural cells.
3. In the present invention, during the culture process, the human cerebral cortical organoid chip can be used to study the effect of drugs on human cerebral cortical organoids by changing the components of the culture medium, and can be widely used in medical research of human cerebral cortical layer and has important significance for drug screening.
4. In the present invention, the printed human cerebral cortical organoid has a structure formed by three layers connected, which realistically imitates the multilayer structure of the real human cerebral cortex, and the organ chip can culture large-scale human cerebral cortical organoids.

BRIEF DESCRIPTION OF THE DRAWINGS

The accompanying drawings constituting a part of the present invention are used to provide a further understanding of the present invention. The exemplary examples of the present invention and descriptions thereof are used to explain the present invention and do not constitute an improper limitation of the present invention. Hereinafter, embodiments of the present invention will be described in detail with reference to the accompanying drawings, wherein.

5

Figure 4B:
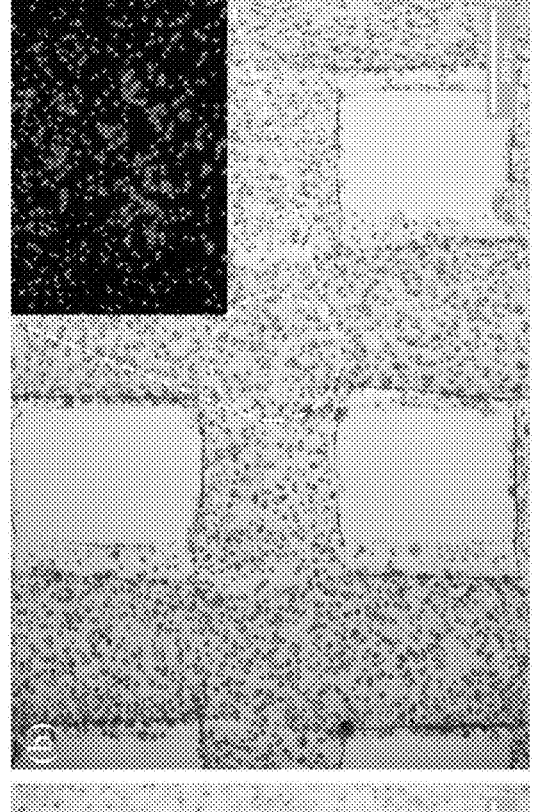
Figure 4A:
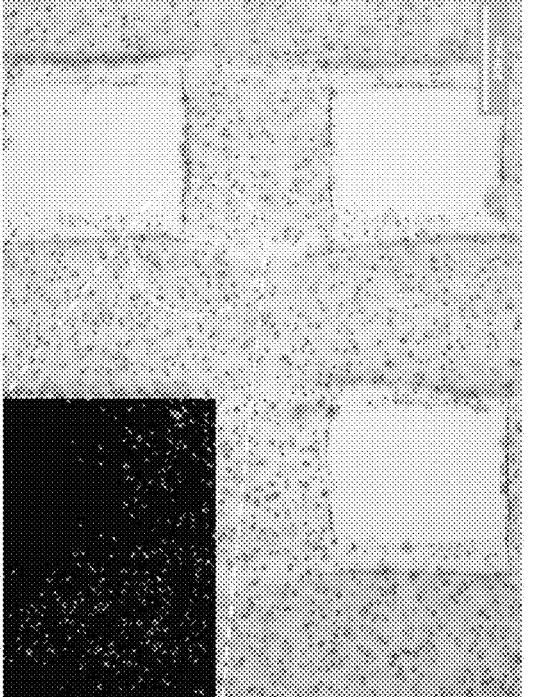
Figure 5:
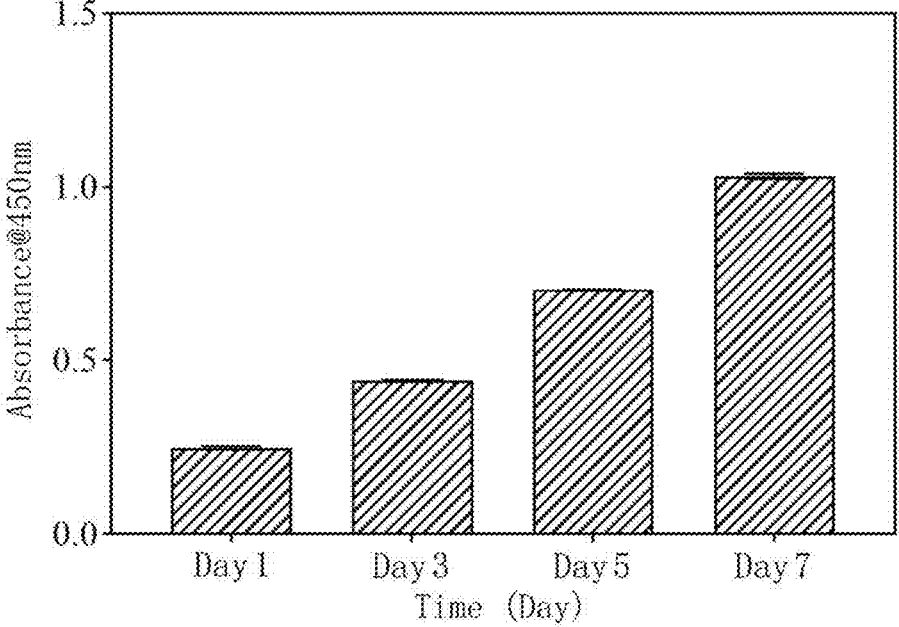

FIG. 4(*a*) is a microscopic image and an immunofluorescence staining image of the printed structure at the first day of culture;

FIG. 4(*b*) is a microscopic image and an immunofluorescence staining image of the printed structure at the seventh day of culture; and FIG. 5 is a CCK8 staining result of the printed structure.

In figures: 1 mixed—flow channel layer, 2—mixed—flow channel, 3—first blind via, 4—liquid pool layer, 5—first through-hole, 6—microporous array layer, 8—human cerebral cortical organoid culture layer, 9—culture chamber, 10—culture medium recovery layer; 11—culture medium recovery pool, 12—stud; 13—second blind via, 14—fourth through-hole, 15—microporous array, 16—third through-hole, 17—second through-hole, 18—culture medium storage pool, 19—culture medium recovery port, 20—culture medium input port.

DETAILED DESCRIPTION

The present invention will be further described below in combination with the specific accompanying drawings and embodiments to enable those skilled in the art to better understand and implement the invention, but the embodiments cited will not be used as a limitation of the invention.

Unless otherwise defined, all technical and scientific terms used herein have the same meaning as those commonly understood by those skilled in the technical field of the present invention. The terms used in the specification of the present invention are only for the purpose of describing specific embodiments and are not intended to limit the present invention. The term "and/or" used herein includes any and all combinations of one or more of the relevant listed items.

Example 1

The present example discloses a human cerebral cortical organoid chip, made of ordinary flat glass, with a size of 50 mm×30 mm×11 mm; the chip needs to be sterilized under 120° C. high temperature and high pressure for 20 min before use.

Figure 1:
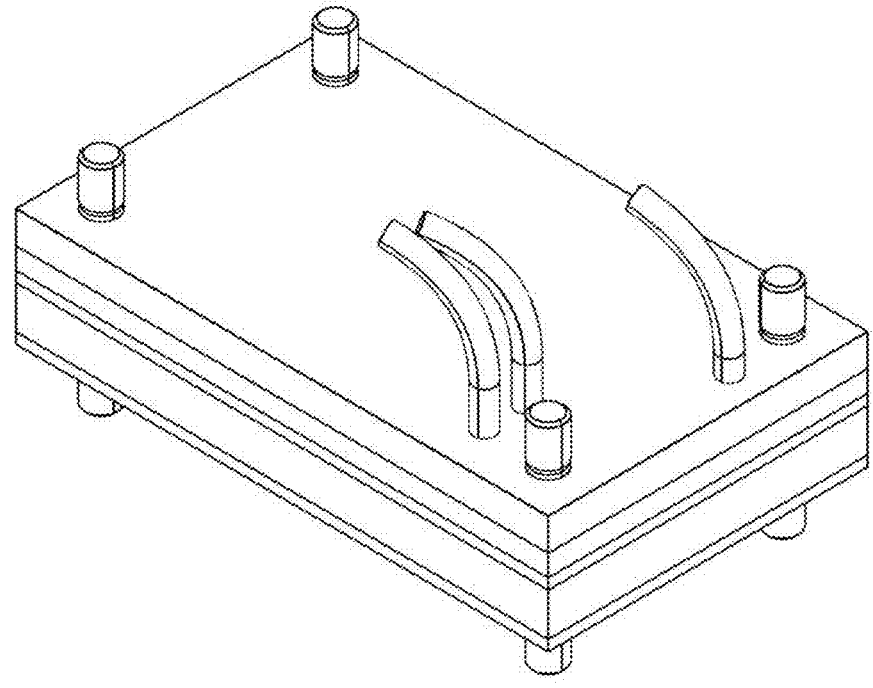
FIG. 1 is a schematic diagram of a structure of a human cerebral cortical organoid chip of the present invention.
Figure 2:
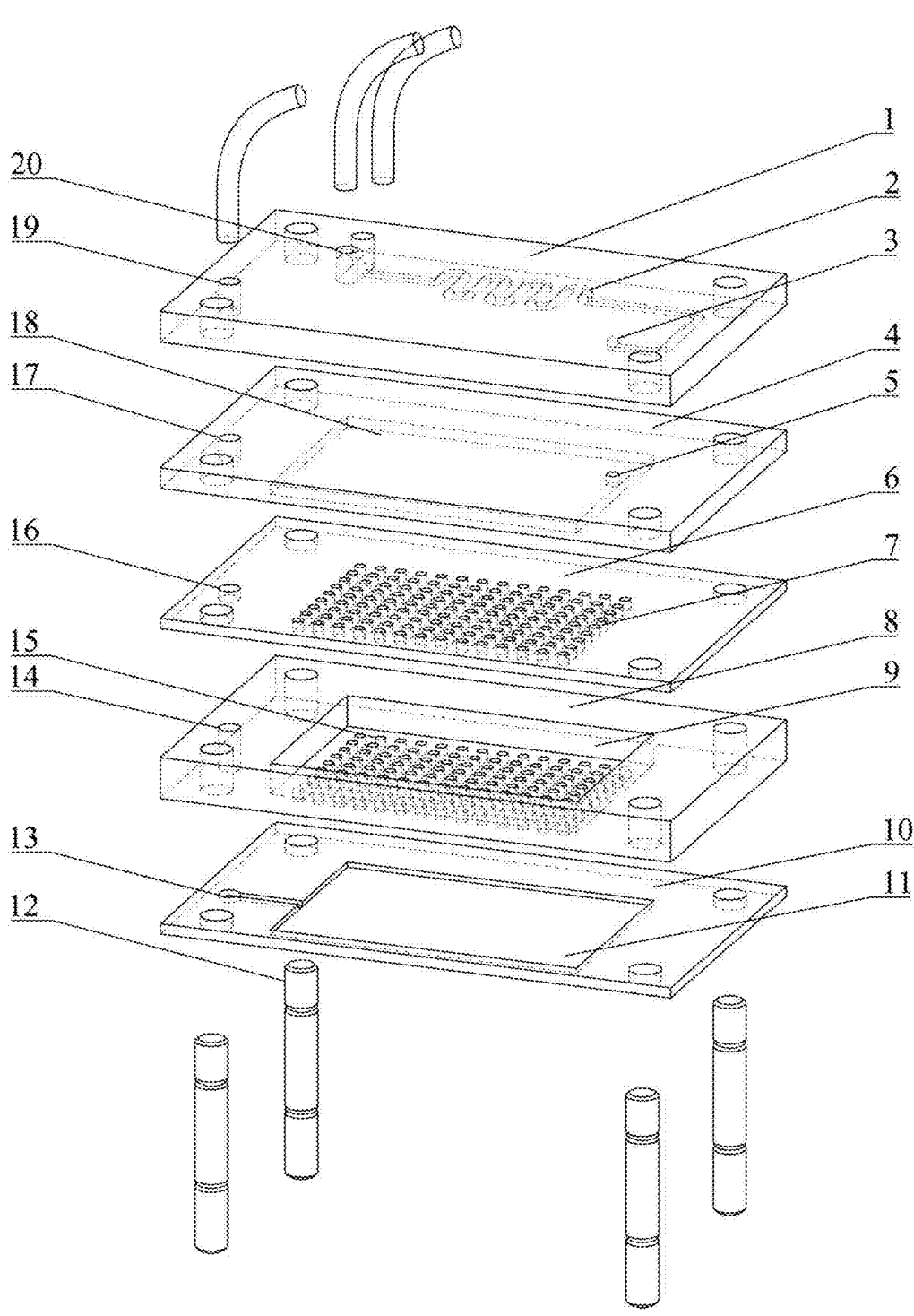
FIG. 2 is an exploded view of the human cerebral cortical organoid chip of the present invention.

As shown in FIGS. 1 and 2, the human cerebral cortical organoid chip comprises a five-layer structure that is sequentially stacked and assembled from top to bottom by a mixed-flow channel layer 1, a liquid pool layer 4, a microporous array layer 6, a human cerebral cortical organoid culture layer 8, and a culture medium recovery layer 10; in particular, rubber sealing rings with same shapes of the layers are sandwiched between the layers of the five-layer structure, and are used for sealing between the layers.

The mixed-flow channel layer 1 comprises a culture medium input port 20, a mixed-flow channel 2, a first blind via 3, and a culture medium recovery port 19; wherein the culture medium input port 20 is used to input the culture medium, and the mixed-flow channel 2 mixes the culture medium of different components evenly and inputs the mixed culture medium to a culture medium storage pool 18 through the first blind via 3;

the liquid pool layer comprises the culture medium storage pool 18, a first through-hole 5, and a second through-hole 17; wherein, the first blind via 3 is connected to the culture medium storage pool 18 through the first through-hole 5, and the microporous array layer 6 communicates the culture medium storage pool 18 with the human cerebral cortical organoid culture layer 8, is used for allowing the culture medium to pass slowly.

the human cerebral cortical organoid culture layer 8 comprises a culture chamber 9, a fourth through-hole 14, and a microporous array 15; the culture chamber 9 is a human cerebral cortical organoid culture chamber.

The culture medium converges from the culture medium input port 20 of the mixed-flow channel layer 1, and flows into the liquid pool layer 4 through the mixed-flow channel 2, at the first blind via 3 and the first through-hole 5, and the culture medium in the liquid pool layer 4 flows into the human cerebral cortical organoid culture layer 8 through the microporous array layer 6.

In particular, an upper surface and a lower surface of the microporous array layer 6 are provided with a porous elastic film for buffering the pressure of the culture medium on the human cerebral cortical organoid.

After passing through the human cerebral cortical organoid culture layer 8, the culture medium flows into the culture medium recovery layer 10 through the microporous array 15 and is recovered through a second blind via 13, the fourth through-hole 14, a third through-hole 16, the second through-hole 17, and the culture medium recovery port 19.

In particular, a slope of a bottom of a culture medium recovery pool 11 is 1°.

Preferably, the material of the human cerebral cortical organoid chip is ordinary flat glass.

Figure 3:
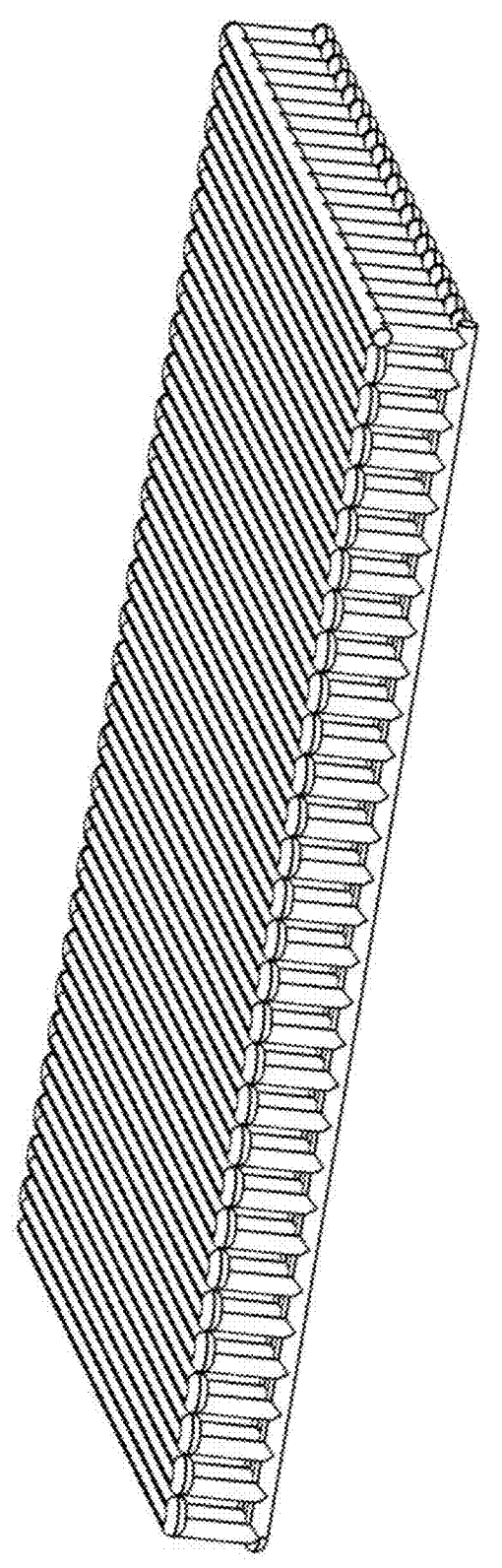
FIG. 3 is a schematic diagram of a structure of a human cerebral cortical organoid of the present invention.

Based on the chip described above, the present example also provides a method of preparing human cerebral cortical organoids using 3D bioprinting method, comprising: first of all, as shown in FIG. 3, the human cerebral cortical organoid in the present example is of a three-layer structure with a size of 30 mm×20 mm×3 mm; wherein, the human cerebral cortical organoid has three layers, a bottom layer thereof is composed of transversely arranged nerve fibers, a middle layer is composed of vertically arranged nerve fiber bundles, a top layer is composed of vertically arranged nerve fiber bundles. A specific method for printing the human cerebral cortical organoid into the chip described above using an extrusion printer, comprising the following steps:

Firstly, sterilizing the human cerebral cortical organoid chip under 120° C. high temperature and high pressure for 20 min, and then drying it;

setting the temperature of a cryogenic platform of a 3D bioprinter to 15° C.; transferring a cell-laden bioink into a syringe of the printer; setting the temperature of the syringe to 26° C., and incubating the bioink for 10 min; and fixing together, by studs 12, and placing the human cerebral cortical organoid culture layer 8 and the culture medium recovery layer 10 on the cryogenic platform of the 3D bioprinter; infusing a gelatin support bath prepared in Example 1 in the culture chamber 9 in the human cerebral cortical organoid culture layer 8. After planning of a printing path is completed, printing directly the human cerebral cortical organoid into the chip.

In particular, a specification of a needle used in printing is 25G, the height of the layer is set to 0.2 mm, the printing speed is set to 100 mm/min, the movement speed is set to 900 mm/min, a shaft return speed is set to 2000 mm/min, a Brim Width is set to 1 mm, a Brim speed is set to 100 mm/min, and a printing pressure is set to 30 kPa.

After the printing is completed, scraping off the excess gelatin support bath with a spatula, and sequentially assembling the microporous array layer 6, the liquid pool layer 4, and the mixed-flow channel layer 1. Introducing the culture medium containing 10% (w/v) fetal bovine serum and 1% (w/v) penicillin/streptomycin to the culture medium input port 20; and, placing the chip in an incubator at 37° C. with 5% $CO_2$ for culturing.

Further, the cell-laden bioink is a composite solution composed of alginate, gelatin, and hyaluronic acid as monomers, and the corresponding preparation method is as follows:

Step 1: dissolving sodium alginate in 1×PBS, stirring at 37° C.-40° C. for 2 h, and degassing using an ultrasonic dispersion instrument to obtain an alginate solution;

Step 2: dissolving gelatin and hyaluronic acid in 1×PBS, stirring at 37° C. for 1 h, and degassing using the ultrasonic dispersion instrument to obtain a gelatin composite solution;

Step 3: irradiating the alginate solution with 260 nm UV light for 24 h to sterilize, and sterilizing by filtration the gelatin composite solution using a 0.22 μm sterilizing filter at 40° C.; and Step 4: mixing the alginate solution with the gelatin composite solution at 37° C. in a 1:1 ratio to obtain a bioink precursor solution, and dispersing the cells evenly into the bioink precursor solution at a density of $1×10^6$ ml$^{-1}$.

In the present example, the preparation of the cell-laden bioink specifically comprises the following steps:

Preparing a cell-laden hydrogel precursor solution:

weighing and dissolving 0.5 g of sodium alginate powder in 10 ml of 1×PBS buffer solution, stirring the solution at 920 r/min for 2 h using a magnetic stirrer, while heating the solution to 40° C. and keeping it at the present temperature until the sodium alginate is completely dissolved to obtain a 5% (w/v) sodium alginate solution; then, degassing the sodium alginate solution for 2 min using an ultrasonic cleaner and then transferring the degassed solution into a clear glass vial and sterilizing it using 260 nm UV light for 24 h; after the sterilization is finished, transferring the glass vial containing the sodium alginate solution to a 4° C. environment for storage;

weighing and dissolving 1.2 g of gelatin powder and 4 mg of hyaluronic acid in 10 ml of 1×PBS buffer solution, and stirring the solution at 700 r/min for 1 h using the magnetic stirrer, while heating the solution to 37° C. and keeping it at the present temperature until the solvent is completely dissolved to obtain a gelatin composite solution; after the stirring is completed, degassing the solution for 2 min using the ultrasonic cleaner and sterilizing by filtration the degassed solution using a 0.22 μm filter;

heating the prepared sodium alginate solution and prepared gelatin composite solution to 40° C. and mixing them in a 1:1 ratio and well using a vortex shaker, and then keeping a bioink precursor solution obtained after the mixing at 40° C. for use; and selecting and culturing NE-4C mouse neural stem cells in a culture medium containing 10% fetal bovine serum, 1% penicillin/streptomycin; maintaining cultures in a humidified incubator at 37° C. with 5% $CO_2$, and changing the culture medium every other day; before preparing the cell-laden bioink, detaching and counting the cells at a cell density of $3×10^6$ ml$^{-1}$; pipetting 2 ml of cell suspension according to a cell density of $1×10^6$ ml$^{-1}$ in the bioink, and centrifuging; pipetting 6 ml of the bioink precursor solution and blowing the cells evenly therein to obtain the cell-laden bioink.

Further, a method of preparing the gelatin support bath described above in the present example is as follows:

measuring out 50 ml of ultrapure water, weighing and dissolving 2.5 g of gelatin granules and 0.5 g of CaCl$_2$) granules into the ultrapure water, stirring the solution at 700 r/min for 1 h using a magnetic stirrer, heating the solution to 37° C. while the stirring; degassing the solution using an ultrasonic cleaner for 2 min after the stirring is completed, to obtain 5% (w/v) gelatin solution, then transferring the obtained gelatin solution to a 50 ml centrifuge tube and incubating the gelatin solution at 4° C. for 24 h to wait for the gelatin to crosslink; weighing and dissolving 3 g of CaCl$_2$ granules in 300 ml of ultrapure water to prepare 1% (w/v) CaCl$_2$) solution; cutting the cross-linked gelatin gel into squares of 10 mm$^3$, and putting the squares into a crusher, with adding the 1% (w/v) CaCl$_2$) solution with 3 times volume, to crush at 10000 r/min for 60 s to obtain a gelatin granule solution; centrifuging the gelatin granule solution using a centrifuge under a centrifugal force of 2000 g, then removing supernatant after centrifugation; adding the 1% (w/v) CaCl$_2$ solution with 3 times volume again, centrifuging and washing the gelatin granules to obtain the gelatin support bath.

Example 2

Based on Example 1, the present example is to perform a cytotoxicity experiment, and a specific process thereof is as follows:

transferring a cell-laden bioink into a syringe of a 3D bioprinter, setting the temperature of the syringe to 26° C., and carrying out the printing after the cell-laden bioink is incubated for 10 min; setting the temperature of a printing platform of the printer to 5° C., a size of a needle of the syringe to 22G, a layer height to 0.3 mm, a printing speed to 100 mm/min, a movement speed to 900 mm/min, a printing pressure to 16 kPa; to print a three-layer grid structure, of which size is 12.0 mm×12.0 mm, a layer height is 0.3 mm, and spacing is 1 mm×1 mm.

After the printing is finished, washing the printed structure—a scaffold—twice using 1×PBS, and transferring the scaffold into a culture medium containing 10% (w/v) fetal bovine serum and 1% (w/v) penicillin/streptomycin for culturing; placing the cultures in an incubator at 37° C., with 5% $CO_2$.

Analyzing the Cell activity using a cell viability/cytotoxicity detection kit on days 1, 3, 5, and 7 of the culture. Carrying out an observation using an inverted fluorescence microscope, as shown in FIG. 4, counting live and dead cells using ImageJ, and obtaining, through the calculation, a survival rate of the cells after the completion of printing is above 96%, which indicated that the printing process had little effect on the cells, and the cells kept high survival rate with the extension of the culture time, and significant proliferation of the cells was seen.

Testing the proliferation status of the cells using a CCK8 kit on days 1, 3, 5, and 7 of the culture. As shown in FIG. 5, the tests on days 1 and 3 after printing showed that an absorbance did not change much and the number of the cells remained approximately the same, mainly due to changes in an extracellular environment during printing. The tests on days 5 and 7 showed that there was a large increase in the absorbance and the large proliferation of the cells, which indicated that the printing process does not cause irreversible damage to the state of the cells and the biomaterials used have good cytocompatibility and may support cell proliferation and migration.

Example 3

Sterilizing human cerebral cortical organoid chips under 120° C. high temperature and high pressure for 20 min and drying the sterilized chips. Printing human cerebral cortical organoids in the human cerebral cortical organoid chip to construct a total of three human cerebral cortical organoid chips A, B, and C. One input port of the human cerebral cortical organoid chip A is connected to a first micro-peristaltic pump for pumping in a complete culture medium for culturing, while the other input port of the chip A is plugged with a small PDMS plug; one input port of the human cerebral cortical organoid chip B is connected to a second micro-peristaltic pump for pumping in complete culture medium added with 10 ng/ml of nerve growth factor (NGF), and the other input port of the chip B is plugged with a PDMS plug; and one input port of the human cerebral cortical organoid chip C is connected to a third micro-peristaltic pump for pumping in complete medium added with a concentration of 10 ng/ml of the NGF, and the other input port of the chip C is fed with gas with a square waveform and a frequency of 60 beats/min.

Taking out the human cerebral cortical organoids from the chips on day 14 of the culture. Carrying out an immunol fluorescence staining on slices of the human cerebral cortical organoids, and measuring the length of the synapse of the neural stem cells using ImageJ to explore the effect of nerve growth factor and pressure on the formation of the synaptic network.

What is claimed is:

1. A human cerebral cortical organoid chip, comprising from top to bottom a mixed-flow channel layer, a liquid pool layer, a microporous array layer, a human cerebral cortical organoid culture layer, and a culture medium recovery layer; wherein, adjacent layers are sealed by a sealing ring;

the mixed-flow channel layer comprises a culture medium input port, a mixed-flow channel, a first blind via, and a culture medium recovery port;

the liquid pool layer comprises a culture medium storage pool, a first through-hole, and a second through-hole; wherein the culture medium input port is used for inputting the culture medium, the mixed-flow channel mixes the different components of culture medium evenly, and the mixed culture medium is inputted into the culture medium storage pool in the liquid pool layer through the first blind via and the first through-hole;

the microporous array layer is provided with a third through-hole;

the human cerebral cortical organoid culture layer comprises a culture chamber, a fourth through-hole, and a microporous array; the culture chamber being a human cerebral cortical organoid culture chamber; the culture medium flows from the culture chamber through the microporous array layer into the medium recovery layer; the microporous array layer is used for allowing the medium to pass; and the culture medium recovery layer is provided with a culture medium recovery pool and a second blind via, and a bottom of the culture medium recovery pool is provided with a slope, and the culture medium passes through the second blind via, the fourth through-hole, the third through-hole, and the second through-hole in turn and then passes through the culture medium recovery port to complete a recovery cycle.

2. The human cerebral cortical organoid chip according to claim 1, wherein a PET porous membrane is covered under the microporous array layer.

3. A method of in situ 3D bioprinting human cerebral cortical organoids in human cerebral cortical organoid chips according to claim 1, comprising: connecting a culture medium recovery layer and a human cerebral cortical organoid culture layer with studs and then fixing them on a printing platform; injecting a gelatin support bath into a culture chamber; storing a cell-laden bioink of the human cerebral cortical organoid in a syringe of a 3D bioprinter; in situ printing the human cerebral cortical organoid in the gelatin support bath in the culture chamber using the 3D bioprinter; and, after the printing is completed, in situ packaging the chip, and then perfusing with a culture medium for culturing.

4. The method of in situ 3D bioprinting human cerebral cortical organoids according to claim 3, wherein, after the printing is completed, scraping off the excess gelatin support bath with a spatula, and sequentially assembling a microporous array layer, a liquid pool layer, and a mixed-flow channel layer; introducing the culture medium into a culture medium input port; and, placing the chip in an incubator for culturing.

5. The method of in situ 3D bioprinting human cerebral cortical organoids according to claim 4, wherein, components of the cell-laden bioink of the human cerebral cortical organoid comprise alginate, gelatin, and hyaluronic acid.

6. The method of in situ 3D bioprinting human cerebral cortical organoids according to claim 5, wherein, a method of preparing the cell-laden bioink for the human cerebral cortical organoid comprises the steps of: dissolving alginate, gelatin, and hyaluronic acid respectively in buffer solutions to obtain a bioink precursor solution, and then dispersing cells evenly into the bioink precursor solution.

7. The method of in situ 3D bioprinting human cerebral cortical organoids according to claim 6, wherein, the method of preparing the cell-laden bioink of the human cerebral cortical organoid specifically comprises:

Step 1: dissolving sodium alginate in 1×PBS (phosphate buffered saline), stirring for a set time at a set temperature, and degassing using an ultrasonic dispersion instrument to obtain an alginate solution;

Step 2: dissolving gelatin and hyaluronic acid in 1×PBS, stirring for a set time at a set temperature, and degassing using the ultrasonic dispersion instrument to obtain a gelatin composite solution;

Step 3: irradiating the alginate solution with ultraviolet (UV) light for a set time to sterilize, and sterilizing by filtration the gelatin composite solution using a sterilizing filter at a set temperature environment; and Step 4: mixing the alginate solution with the gelatin composite solution at a set temperature in a 1:1 ratio to obtain the bioink precursor solution, and dispersing the cells evenly into the bioink precursor solution to obtain the cell-laden bioink.

8. A human cerebral cortical organoid obtained by a method of in situ 3D bioprinting human cerebral cortical organoids according to claim 3, comprising a structure formed by three layers connected, wherein the top layer is a tissue plate with nerve fibers arranged longitudinally, the middle layer is a nerve fiber bundle, and the bottom layer is a nerve tissue plate with nerve fibers arranged transversely.

* * * * *